United States Patent
Clouatre et al.

(10) Patent No.: US 6,482,858 B1
(45) Date of Patent: Nov. 19, 2002

(54) (−)-HYDROXYCITRIC ACID FOR WOUND HEALING AND IMMUNOMODULATION

(76) Inventors: Dallas L Clouatre, 555 Bryant St., #357, Palo Alto, CA (US) 94301-1704; James M Dunn, 3236 Hinsdale Pl., Littleton, CO (US) 80112

( * ) Notice: Subject to any disclaimer, the term of this patent is extended or adjusted under 35 U.S.C. 154(b) by 0 days.

(21) Appl. No.: 09/886,572

(22) Filed: Jun. 20, 2001

(51) Int. Cl.$^7$ ............................................. A61K 31/194
(52) U.S. Cl. ..................................................... 514/574
(58) Field of Search ......................................... 514/574

(56) References Cited

U.S. PATENT DOCUMENTS

| | | | |
|---|---|---|---|
| 3,764,692 A | 10/1973 | Lowenstein .................. | 424/279 |
| 3,767,678 A | 10/1973 | Guthrie et al. ............ | 260/343.6 |
| 3,919,254 A | 11/1975 | Guthrie et al. ............ | 260/343.6 |
| 3,993,668 A | 11/1976 | Guthrie et al. ............ | 260/343.6 |
| 4,443,619 A | 4/1984 | Guthrie et al. .............. | 549/518 |
| 5,626,849 A | 5/1997 | Hastings et al. .......... | 424/195.1 |
| 5,656,314 A | 8/1997 | Moffett et al. .............. | 426/271 |
| 5,783,603 A | 7/1998 | Majeed et al. .............. | 514/574 |
| 5,911,992 A | 6/1999 | Braswell et al. .......... | 424/195.1 |
| 5,914,326 A | 6/1999 | McCarty et al. ............. | 514/188 |
| 6,207,714 B1 | 3/2001 | Clouatre et al. ............ | 514/574 |
| 6,217,898 B1 | 4/2001 | Cavazza ...................... | 424/450 |
| 6,221,901 B1 | 4/2001 | Shrivastava et al. ........ | 514/458 |

OTHER PUBLICATIONS

Bitar MS, et al. Glucocorticoid–Dependent Impairment of Wound Healing in Experimental Diabetes: Amelioration by Adrenalectomy and RU 486. Journal of Surgical Research 1999;82:234–243.

Bitar MS, et al. Insulin and glucocorticoid–dependent suppression of the IGF–I system in diabetic wounds. Surgery 2000;127:687–95.

Cagnacci A, Soldani R, Yen SS. Melatonin enhances cortisol levels in aged women: reversible by estrogens. J. Pineal Res Mar. 1997;22(2):81–5.

Cagnacci A, Soldani R, Yen SS. Melatonin enhances cortisol levels in aged but not young women. Eur J Endocrinol Dec. 1995;133(6):691–5.

Clouatre D, Rosenbaum M. The Diet and Health Benefits of HCA, Keats Publishing 1994.

Clouatre D, Lewis A. Melatonin and the Biological Clock. Keats, 1996.

Denda M, et al. Stress alters cutaneous permeability barrier homeostasis. Am. J. Physiol. Reguatory Integrative Comp. Physiol. 2000;278:R367–R372.

Elenkov IJ. Stress, cytokine patterns and susceptibility to disease. Bailliére's Clinical Endocrinology and Metabolism 1999;13,4:583–595.

Ferrari E, Arcaini A, Gornati R, Pelanconi L, Cravello L, Fioravanti M, Solerte SB, Magri F. Pineal and pituitary–adrenocortical function in physiological aging and in senile dementia. Exp. Gerontol Dec. 2000;35(9–10):1239–50.

Greenwood MR, Cleary MP, Gruen R, Blase D, Stern JS, Triscari J, Sullivan AC. Effect of (−)–hydroxycitrate on development of obesity in the Zucker obese rat. Am J Physiol. Jan. 1981;240(1):E72–8.

Hultsch T, et al. Ascomycin macrolactam derivative SDZ ASM 981 inhibits the release of granule–associated mediators and of newly synthesized cytokines in RBL 2H3 mast cells in an immunophilin–dependent manner. Arch Dermatol Res Sep. 1998;290(9):501–7.

Ishihara K, Oyaizu S, Onuki K, Lim K, Fushiki T. Chronic (−)–hydroxycitrate administration spares carbohydrate utilization and promotes lipid oxidation during exercise in mice. J Nutr. Dec. 2000;130(12):2990–5.

Kellner M, et al. Corticotropin–releasing hormone inhibits melatonin secretion in healthy volunteers—a potential link to low–melatonin syndrome in depression? Neuroendocrinology Apr. 1997;65(4):284–90.

Kos–Kudla B, et al. Diurnal Rhythm of Serum Melatonin, ACTH And Cortisol In Asthma Patients with Long Term Glucocorticoid Treatment. Endocrine Regulations 1997;31:47–54.

Laue L, et al. Effect of chronic treatment with the glucocorticoid antagonist RU 486 in man: toxicity, immunological, and hormonal aspects. J Clin Endocrinol Metab Dec. 1990;71(6):1474–80.

McCarty MF. Promotion of hepatic lipid oxidation and gluconeogenesis as a strategy for appetite control. Medical Hypotheses 1994;42:215–225.

Messiha FS. Fluoxetine: Adverse effects and drug–induced interactions. Clinical Toxicology 1993;31(4):603–630.

Mozzanica N, et al. Plasma melatonin levels in psoriasis. Acta Derm Venereol 1988;68(4):312–6.

Sullivan AC, Triscari J. Metabolic regulation as a control for lipid disorders. I. Influence of (−)–hydroxycitrrate on experimentally induced obesity in the rodent. American Journal of Clinical Nutrition 1977;30:767–776.

Sullivan, Ann C. and Joseph Triscari. Possible interrelationship between metabolite flux and appetite. In D. Novin, W. Wyriwicka and G. Bray, eds., Hunger: Basic Mechanisms and Clinical Implications (New York: New Raven Press, 1976) 115–125.

Sullivan AC, Gruen RK. Mechanisms of appetite modulation by drugs. Federation Proceedings 1985;44,1:139–144.

*Primary Examiner*—Phyllis G. Spivack

(57) ABSTRACT

HCA Supplementation improves wound healing and immunomodulation/immunoregulation, including improving depressed immune function and also reducing excessive immune activity such as is found in elevated humoral immunity linked to allergies and autoimmune diseases. The benefits of HCA are especially pronounced with the use of the preferred salt of the acid, potassium hydroxycitrate, and may be further potentiated by the use of a controlled-release form of the compound.

12 Claims, No Drawings

(−)-HYDROXYCITRIC ACID FOR WOUND HEALING AND IMMUNOMODULATION

BACKGROUND OF THE INVENTION

1. Field of the Invention

This invention relates to pharmaceutical compositions containing (−)-hydroxycitric acid useful for wound healing and immunomodulation, especially by means of correcting the dysregulation of glucocorticoid and melatonin metabolism.

2. Description of Prior Art

The immune system is the body's ultimate defense against attack by external pathogens, such as bacteria and viruses, and against internal mistakes in replication, such as cancer. Modern medicine for the most part seeks to bolster this defense in only two ways. First, it employs a wide range of supplements to the body's own protective mechanisms in the form of drugs and therapies. Antibiotics, chemotherapy and radiation therapy all attempt to aid or even to replace the body's own defenses when these prove inadequate. Second, medicine uses vaccinations to bolster the immune system's specific abilities, usually in advance of exposure to a pathogen or as an aid to help the body target specific pathogens which the immune system either does not recognize or does not react strongly enough against.

More recently, researchers have begun to reproduce elements of the immune system and to use these against diseases, especially cancer. For instance, genetically engineered bacteria can now produce interferon, which can be harvested and then injected into the patient's blood or even directly into a tumor. To date, the results of such methods have been promising, but clinical trials have yielded many fewer complete successes than originally had been hoped for. The reasons for this are not entirely understood, but apparently exogenous sources of immune elements, such as interferon or interleukin-1, are rapidly cleared from the body. Moreover, the immune system is homeostatic—in a healthy immune system, the elements are always in balance with one another. The increase in one aspect of the system typically suppresses some other part of the system. Similarly, the use of antibiotics and other drugs which are powerful supplements to and even substitutes for the body's own functions is medically recognized to suppress natural immunity, in some cases to the point of complete failure.

The quality of the immune response makes itself known in a variety of ways, some of which are readily observable. For instance, one way of looking at the skin is as an immune organ which is in need of constant maintenance and repair. An obvious example of this is to be seen in the case of a cut or scratch. The better the immune system, the faster the healing, but what does healing mean to the skin? It means both preventing infection and returning to its previous condition. Hence, the immune system not only attacks external invaders, but also activates the skin cells called fibroblasts, which are responsible for production of the precursors of collagen, elastin and other elements of the skin and connective tissues. Either improper immune activation or suppression may lead to undesirable effects upon the body's external immune barrier. In the case of the skin, as in other areas of the body, proper immune metabolism is always an issue of balance.

Immune imbalance is readily apparent in conditions such as diabetes mellitus. Diabetics are often troubled by non-healing skin ulcers. Indeed, nonhealing wounds constitute a major problem which plagues approximately 15% of all patients with diabetes despite proper insulin treatment and following a prescribed diet. Faulty wound healing contributes to more inpatient hospital days than any other complication associated with diabetes and is a factor in 81% of diabetic lower extremity amputations. Experimental and clinical studies using various models of wound healing reveal that diabetes is accompanied by a derangement in tissue repair involving almost every element of wound healing, including inflammation, cellular proliferation, and angiogenesis. In addition, reduced collagen formation and lower tensile strength have also been reported in surgical diabetic wounds. (Bitar M S, et al. Glucocorticoid-Dependent Impairment of Wound Healing in Experimental Diabetes: Amelioration by Adrenalectomy and RU 486. Journal of Surgical Research 1999;82:234–243.)

Data from various studies show that therapeutic doses of glucocorticoids (GCs) reduce wound healing potential in human and experimental models of wound repair. This inhibition is linked to a delay in the appearance of inflammatory cells and to a reduction in fibroplasia, with a similar delay in the appearance of new connective tissue matrix, collagen synthesis and deposition. An inverse relationship has been shown to exist between wound healing potential and stress, a source of endogenous CGs. Moreover, other findings support the hypothesis that hypercortisolemia is a common feature in both human and experimental diabetes. Blockading GC receptors with the receptor blocker mifepristone (RU486) has shown therapeutic potential in reversing the GC-induced wound healing impairment. (Bitar M S, et al. 1999; Bitar M S, et al. Insulin and glucocorticoid-dependent suppression of the IGF-I system in diabetic wounds. Surgery 2000;127:687–95.)

As in diabetic wound healing deficiency, studies have demonstrated that psychological stress perturbs cutaneous (skin) permeability barrier homeostasis. Research supports the concept that psychological stress is an important determinant of the onset and severity of skin diseases such as psoriasis and adult atopic dermatitis. An increase in endogenous glucocorticoid production, which is deleterious to barrier function, is essential for the barrier abnormalities that occur in response to psychological stress. (Denda M, et al. Stress alters cutaneous permeability barrier homeostasis. Am. J. Physiol. Regulatory Integrative Comp. Physiol. 2000;278:R367–R372.)

A great deal of evidence, again, supports the contention that the actions of glucocorticoids extend far beyond the inhibition of wound healing, the inhibition of fibroblasts, the loss of collagen and connective tissue, and interference with other elements operative at levels beyond that of the skin. An array of findings now indicate that glucocorticoids and catecholamines—the end-products of the stress system—and histamine—a product of activated mast cells—might selectively suppress cellular immunity and favor humoral immune responses. This is mediated by a differential effect of stress hormones and histamine on T helper 1 (Th1)/Th2 patterns and type 1/type 2-cytokine production. Systemic stress appears to induce a Th2 shift, and under certain conditions, it might induce pro-inflammatory activities through neural activation of the peripheral corticotropin-releasing factor-mast cell-histamine axis. Through these mechanisms, stress may influence the onset and/or course of infectious, autoimmune/inflammatory, allergic and neoplastic diseases. (Elenkov I J. Stress, cytokine patterns and susceptibility to disease. Bailliére's Clinical Endocrinology and Metabolism 1999;13,4:583–595.)

The administration of exogenous glucocorticoids clearly dysregulates the physiologic axis involving melatonin, ACTH and cortisol. (Kos-Kudla B, et al. Diurnal Rhythm of Serum Melatonin, ACTH And Cortisol In Asthma Patients with Long Term Glucocorticoid Treatment. Endocrine Regulations 1997;31:47–54.) Interactions between the hypothalamic-pituitary-adrenocortical (HPA) system and melatonin secretion have been demonstrated repeatedly. Unfortunately, most research in this area has been upon melatonin, and only the effects of melatonin on the activity of the HPA system have been studied extensively in man. Evidence to date suggests that the impact of glucocorticoids upon melatonin secretion may be indirect rather than direct. For example, corticotropin-releasing hormone (CRH), which is thought to be involved in HPA abnormalities in depressed patients, can suppress melatonin secretion in healthy in normal volunteers. (Kellner M, et al. Corticotropin-releasing hormone inhibits melatonin secretion in healthy volunteers—a potential link to low-melatonin syndrome in depression? Neuroendocrinology April 1997;65(4):284–90.) As indicated in the preceding paragraph, it is already established that stress can induce CRH peripherally, and therefore a mechanism is known for linking stress/glucocorticoids to reduced and/or dysregulated melatonin release.

Endogenous glucocorticoid levels typically increase and/or become markedly dysregulated as humans age and they remain chronically elevated and/or dysregulated in comparison with the levels found in young adults. According to various studies, a significant increase of serum cortisol levels during evening- and night-times is found in elderly subjects when compared to young controls. Similarly, the circadian amplitude of the cortisol rhythm is significantly reduced in relation to age. More generally, the sensitivity of the hypothalamic-pituitary-adrenal axis to steroid feedback is significantly impaired in elderly subjects. (Ferrari E, et al. Pineal and pituitary-adrenocortical function in physiological aging and in senile dementia. Exp Gerontol December 2000;35(9–10):1239–50.)

Unfortunately, the options for reducing the elevated or dysregulated glucocorticoid levels characteristic of advancing age and, likewise, prolonged stress, are limited. One powerful antagonist to glucocorticoids is mifepristone, the drug RU 486 now being used as the "morning after" pill to prevent conception. This compound does not appear to be appropriate for chronic ingestion. The reasons are clear from a trial which studied 11 healthy male normal volunteers who received RU 486 (10 mg/kg.day) or placebo vehicle, divided into 2 daily oral doses, for 7–14 days. Blood samples were collected every 2 days for measurement of plasma ACTH and cortisol concentrations along with 24-h urine samples for measurement of 17-hydroxysteroid and free cortisol excretion. Complete and differential blood counts, erythrocyte sedimentation rates, C-reactive protein, antinuclear antibodies, rheumatoid factor, and quantitative immunoglobulins were also determined at 2-day intervals. Leukocytes were obtained by leukopheresis for phenotypic characterization and functional analysis before and 7 days after the initiation of RU 486 or placebo therapy. Blockade of cortisol receptors with RU 486 was associated with marked compensatory elevations of plasma ACTH and cortisol and increases in 24-h urinary excretion of 17-hydroxysteroids and free cortisol. Unexpectedly, 8 of the 11 subjects developed generalized exanthem (skin rash) after 9 days of RU 486 treatment. One subject developed symptoms and signs consistent with the diagnosis of adrenal insufficiency, a finding quite in line with the compensatory adrenal secretions found in these volunteers. Total white blood cell counts, absolute lymphocyte, neutrophil and eosinophil counts, erythrocyte sedimentation rate, and quantitative immunoglobulins did not change with RU 486 therapy. Similarly, T-, B-, and natural killer cell subsets did not change during RU 486 treatment. Furthermore, functional evaluation of lymphocyte cytotoxicity and proliferation revealed no changes. The authors concluded that administration of high doses of RU 486 to normal volunteers does not result in measurable enhancement of immune function. However, it should be noted that although RU 486 blocks some glucocorticoid receptor site actions, but it does not lower the levels of glucocorticoids themselves and it does not reduce the levels of secondary effectors, i.e., it does not reduce the levels of ACTH, etc. (Laue L, et al. Effect of chronic treatment with the glucocorticoid antagonist RU 486 in man: toxicity, immunological, and hormonal aspects. J Clin Endocrinol Metab December 1990;71(6):1474–80.)

Another antagonist to the glucocorticoids—seemingly the "natural" choice—is the pineal hormone melatonin taken orally. Paradoxically, however, in some populations, such as in postmenopausal women, oral melatonin treatment increases rather then decreases cortisol levels. (Cagnacci A, et al. Melatonin enhances cortisol levels in aged women: reversible by estrogens. J Pineal Res March 1997;22(2):81–5; Cagnacci A, et al. Melatonin enhances cortisol levels in aged but not young women. Eur J Endocrinol December 1995;133(6):691–5.) Along these same lines, exogenously derived melatonin can increase body serotonin levels and alter the endogenous circadian rhythm of release in various hard-to-control ways and with side effects which climb with the dosage. Melatonin has virtually no possible acute toxicity, but this does not mean that it presents no problems as a supplement. One can argue that the attempt to employ melatonin for its supposed direct effects, such as immune stimulation, rather than its indirect effect via the resetting of the body's internal clock, has been a major error. (Clouatre D, Lewis A. Melatonin and the Biological Clock. Keats, 1996.) In fact, despite its initial vast popularity in the American health food market, oral melatonin supplementation apparently has not lived up to its billing as the premier anti-aging supplement.

Moreover, increases in serotonin from exogenous sources (melatonin, 5-HTP, etc.) are undesirable in many conditions, such as atopic dermatitis and psoriasis, or, indeed, in inflammatory and autoimmune states almost universally. Mast cells play an important role in the pathological development of many inflammatory and allergic diseases; whereas inhibition of mast cell activation is a potential target for therapeutic intervention, preformed mediators (e.g. serotonin) can have adverse effects. (Hultsch T, et al. Ascomycin macrolactam derivative SDZ ASM 981 inhibits the release of granule-associated mediators and of newly synthesized cytokines in RBL 2H3 mast cells in an immunophilin-dependent manner. Arch Dermatol Res September 1998;290 (9):501–7.) More generally, it might be said that precursors to serotonin and drugs which have serotogenic primary mechanisms of action, such as the selective serotonin uptake inhibitors, typically have very significant drawbacks and side effects.

Psoriasis offers yet another way of envisioning the relationship of glucucocorticoids to both melatonin secretion and immune modulation. A daily rhythm of melatonin secretion, with high plasma values during the dark period, has been found in all vertebrates studied so far. In psoriatics, several hormones, including growth hormone (GH) and prolactin, exhibit an altered chronobiology, and some studies in humans indicate that melatonin affects the levels of GH and prolactin. Investigation of the circadian melatonin rhythm in 13 male psoriatics and 13 healthy males measured the levels of melatonin in plasma. Samples were taken at 6 a.m., 8 a.m., 12.00, 4 p.m., 8 p.m. and 2 a.m. Differences in (mean +/−SD) plasma melatonin levels were analyzed by Student's t-test. The results show that psoriatic patients had lost the nocturnal peak and usual circadian rhythm of melatonin secretion. Levels of melatonin were significantly lower than in controls at 2 a.m., and higher at 6 and 8 a.m. and at 12 noon. (Mozzanica N, et al. Plasma melatonin levels in psoriasis. Acta Derm Venereol 1988;68(4):312–6.) This dysregulation in the timing of melatonin secretion mirrors the dysregulation of cortisol circadian rhythms found with advancing age and under conditions of chronic stress.

Unrelated to wound healing, immunoregulation, and to glucocorticoid control according to published literature are the actions of (−)-hydroxycitric acid. Instead, (−)-hydroxycitric acid (abbreviated herein as HCA), a naturally-ocurring substance found chiefly in fruits of the species of Garcinia, and several synthetic derivatives of citric acid have been investigated extensively in regard to their ability to inhibit the production of fatty acids from carbohydrates, to suppress appetite, and to inhibit weight gain. (Sullivan A C, Triscari J. Metabolic regulation as a control for lipid disorders. I. Influence of (−)-hydroxycitrrate on experimentally induced obesity in the rodent. American Journal of Clinical Nutrition 1977;30:767.)

Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffmann-La Roche, have been summarized in at least two United States Patents. In U.S. Pat. No. 5,626,849 these mechanisms are given as follows: "(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . " U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty M F. Promotion of hepatic lipid oxidation and gluconeogenesis as a strategy for appetite control. Medical Hypotheses 1994;42:215–225) is maintained in U.S. Pat. No. 5,914,326.

Almost all of the primary research performed on HCA was carried out by Hoffman-La Roche nearly three decades ago. The conclusion of the Roche researchers was that "no significant differences in plasma levels of glucose, insulin, or free fatty acids were detected in (−)-hydroxycitrate-treated rats relative to controls. These data suggest that peripheral metabolism, defined in the present context as metabolite flux, may be involved in appetite regulation . . . " (Sullivan, Ann C. and Joseph Triscari. Possible interrelationhip between metabolite flux and appetite. In D. Novin, W. Wyriwicka and G. Bray, eds., Hunger: Basic Mechanisms and Clinical Implications (New York: Raven Press,1976) 115–125.) No Roche data was ever published linking HCA to changes in glucocorticoid levels. No conclusions were ever presented which suggested that HCA is useful in preventing bone loss.

Some early preliminary work showed that labeled $^{14}C$ attached to HCA found its way into the brain. (Sullivan A C, Triscari J. Metabolic regulation as a control for lipid disorders. I. Influence of (−)-hydroxycitrrate on experimentally induced obesity in the rodent. American Journal of Clinical Nutrition 1977;30:767.) However, work published by the same authors at a later date indicated otherwise. "Hydroxycitrate, chlorocitrate, and epoxyaconitate, compounds that are structurally similar to the tricarboxylic acid cycle intermediate citric acid, but that differ markedly in biochemical activity, have recently been evaluated in animals for effects on appetite. Because neither these compounds nor their metabolites enter the brain, their primary effects on food intake occur by peripheral mechanisms." (Sullivan A C, Gruen R K. Mechanisms of appetite modulation by drugs. Federation Proceedings 1985;44, 1:139–144.)

The present inventors have discovered that HCA not only reduces glucocorticoid levels in animals, but also, and probably as a direct result, improves the signs of wound healing and immunomodulation/immunoregulation, which is to say that HCA can improve depressed immune function and also reduce excessive immune activity, especially that which involves humoral immunity. Further evidence suggests that HCA improves melatonin metabolism with its concomitant effects upon growth hormone release through non-serotogenic mechanisms. One sign of these benefits, improved protein retention in animals under stressful conditions, has been found to be true in young rats ingesting a 70% glucose diet and, similarly, in middle-aged rats consuming a diet in which 30% of the energy is derived from fats, i.e., a diet more typical of human beings.

Of the readily available forms of HCA, only the potassium and sodium salts of HCA are absorbed well enough to be effective agents at tolerable levels of ingestion. Reasons for this are given in the inventors' copending U.S. Patent Application "Potassium (−)-Hydroxycitric Acid Methods For Pharmaceutical Preparations For Stable And Controlled Delivery." Derivatives of HCA may also be active and effective in this regard. (U.S. Pat. Nos. 3,993,668; 3,919, 254; 3,767,678.) Liquid forms of HCA currently in use are irritating to the digestive system, depending upon the dose, and may cause an elevation of stress hormones as a result. Researchers have found that animals given high doses of the liquid form of the compound orally exhibit stress behavior. (Ishihara K, et al. Chronic (−)-hydroxycitrate administration spares carbohydrate utilization and promotes lipid oxidation during exercise in mice. J Nutr. December 2000;130(12):2990–5.) Similarly, the ethylenediamine salts of HCA used in some of the later research performed by Hoffman-La Roche are known to be irritating and even toxic, properties which are due to the ethylenediamine ligand and not to the HCA. In contrast to the quite limited efficacy found with the calcium salt and some other delivery forms of HCA, the impact of ingestion of appropriate amounts of the appropriate salts of HCA in reducing glucocorticoid levels has been shown to be powerfully statistically significant.

Therefore, the current invention teaches that HCA supplementation constitutes a novel means of reducing age-related and stress-related glucocorticoid dysregulation. Supplementation improves wound healing and immunomodulation/immunoregulation, including improving depressed immune function and also reducing excessive immune activity, including humoral immunity. Further evidence suggests that HCA improves melatonin metabolism with its concomitant effects upon growth hormone release through non-serotogenic mechanisms.

SUMMARY OF THE INVENTION

The inventors have discovered that HCA supplementation constitutes a novel means of reducing age-related and stress-related glucocorticoid dysregulation. Supplementation improves wound healing and immunomodulation/immunoregulation, including improving depressed immune function and also reducing excessive immune activity such as is found in elevated humoral immunity linked to allergies and autoimmune diseases. Further evidence suggests that HCA improves melatonin metabolism with its concomitant effects upon growth hormone release through non-serotogenic mechanisms. These action by HCA have not heretofore been recognized. The benefits of HCA are especially pronounced with the use of the preferred salt of the acid, potassium hydroxycitrate, and may be further potentiated by the use of a controlled-release form of the compound. The discovery that HCA has stress-moderating and immunomodulating effects allows for the creation of novel and more efficacious approaches for improving healing (for instance, of diabetic skin ulcers) even in the face of diet and exercise habits which are less than ideal and in the face of chronic stress. Furthermore, this discovery makes possible the development of adjuvant modalities which can be used to improve the results realized through the employment of more conventional remedies. HCA delivered in the form of its potassium salt is efficacious at a daily dosage (bid or tid) of between 750 mg and 10 grams, preferably at a dosage of between 3 and 6 grams for most individuals. A daily dosage above 10 grams might prove desirable under some circumstances, such as with grossly obese or resistant individuals, but this level of intake is not deemed necessary under normal conditions.

Objects and Advantages

It is an objective of the present invention to provide a novel means of reducing the age-, stress and diabetes-related loss in glucocorticoid regulation as this applies to wound healing, immune function and melatonin metabolism. Elevated and dysregulated glucocorticoid levels from other causes also potentially may be ameliorated. The present invention has the advantages of safety and absence of side effects (Clouatre D, Rosenbaum M. The Diet and Health Benefits, Keats Publishing 1994), claims not true of treatment with the current drugs available, such as RU 486. The glucocorticoid mechanisms influenced by HCA supplementation are returned to levels and responses more typical of young adults, hence the inherent tolerability of HCA as a preventative and corrective treatment. Knowledge of the present invention has the advantage of allowing the use of forms of (−)-hydroxycitric acid, including especially through controlled release formulations, as adjuvants to current drugs designed to reduce the consequences of stress, improve wound healing, to modulate immune function and improve melatonin/growth hormone metabolism.

It should be noted that HCA offers several advantages over the ingestion of exogenous melatonin and growth hormone releasers (large amounts of specific amino acids taken at specified times on an empty stomach). Exogenous melatonin can disrupt the circadian rhythm, lose effectiveness with continued use, worsen autoimmune and inflammatory conditions, and, because it can increase serotonin, actually worsen some forms of depression. Excessive melatonin ingestion also can lead to a "hang-over" type of drowsiness the following day, to nasal congestion (serotonin-related), and to feelings of being "off," (again, likely serotonin-related). Because melatonin can induce growth hormone spikes, it may not be appropriate for use by diabetics. Melatonin precursors, for instance, 5-HTP, can alter brain serotonin levels and may suffer from many or all of the drawbacks which are true of supplementation with melatonin.

Growth hormone releasers, similarly, may oppose the actions of insulin and increase the loss of potassium, hence are inappropriate for use by diabetics and borderline diabetics. Two common supposed GH releasers, the amino acids L-arginine and L-ornithine, may either improve or worsen the condition of diabetics, may reactivate latent herpes virus infections, and may worsen certain types of psychoses. Amino acid GH releasers/inducers, moreover, appear to work best in the young, who do not need addition GH release, but to have little or no effect in most individuals middle-aged or older. As is true of the age issue with these compounds, they also appear to be more effective in those who are healthy (and therefore have less need) than in those who are less healthy (and therefore more in need of increased GH release).

The effect of HCA upon melatonin and growth hormone metabolism appears to be primarily or even entirely indirect. Improved regulation of total glucocorticoid levels and the timing of peak levels has the effect of quite naturally returning the body to its capacity for recovery found in young adulthood. Therefore, with HCA there is no disruption of circadian cycles, no production of excess serotonin, and so forth. Instead, because the body's chronic levels of circulating glucocorticoids has been brought back into a more acceptable range, interactions between the hypothalamic-pituitary-adrenocortical (HPA) system and melatonin secretion can be normalized and the responsiveness of this axis to corticoid stimulation and feedback, likewise, can be returned to more advantageous levels.

DESCRIPTION OF THE PREFERRED EMBODIMENTS

The free acid form and various salts of (−)-hydroxycitric acid (calcium, magnesium, potassium, sodium and mixtures of these) have been available commercially for several years. Any of these materials can be used to fulfill the invention revealed here, but with varying degrees of success. For reasons given in our co-pending U.S. Patent Application "Potassium (−)-Hydroxycitric Acid Methods For Pharmaceutical Preparations For Stable And Controlled Delivery," these materials are generally useful in this descending order of efficacy: potassium salt, sodium salt, free acid, magnesium salt, calcium salt. A novel method for improving the efficacy and workability of these forms is provided in that application. Exact dosing will depend upon the form of HCA used, the weight of the individual involved, and the other components of the diet. In part due to the need to control the release of this hypoglycemic agent in diabetics, as outlined in the inventors' recently accepted U.S. Pat. No. 6,207,714 covering the employment of HCA as hypoglycemic agent, a controlled release preparation is to be preferred. Controlled release can also be expected to improve results by aiding in maintaining a sustained exposure to the drug as required for therapy.

The previously patented hydroxycitric acid derivatives (mostly amides and esters of hydroxycititric acid, the patents for which are now expired, to wit, U.S. Pat. Nos. 3,993,668; 3,919,254; and 3,767,678) likely are roughly equivalent to the HCA sodium salt in efficacy and can be applied as taught herein by one skilled in the art. However, for the purposes of reducing stress hormone (glucocorticoid) levels, hydroxycitric acid in its free acid form and in its lactone form may prove to be the least desirable of currently available versions of the compound. The free acid and the lactone forms are irritating to the gastrointestinal tract and thus, in the higher dosages required for therapy, may lead to elevations in stress response. Likewise, hydroxycitric acid in its free acid form and in its lactone form may be less desirable for long term use due to their ability to chelate minerals and thereby perhaps lead to mineral loss.

EXAMPLE 1

Effects Upon Glucocorticoid Levels

To test the properties of HCA in various forms under conditions similar to those found in human clinical trials, the inventors arranged for male OM rats aged 10 weeks to be fed a diet in which 30% of the calories were obtained from fat under standard conditions. The rats were intubated twice daily with one of three HCA salts or placebo. The amount of HCA in each arm of 5 animals was the minimum dosage which had been found effective in the form of the pure trisodium salt of HCA in tests by Hoffmann-La Roche in animals ingesting a 70% glucose diet, i.e., 0.33 mmoles/kg body weight HCA given twice per day. The HCA salts used were these: CaKHCA=a mixed calcium and potassium HCA salt commercially marketed as being entirely water soluble; KHCA 1=a relatively clean, but still hardly pure potassium salt of HCA with a good mineral ligand attachment supplying 4467 mg potassium/100 grams of material; KHCA 2=an impure potassium salt of HCA with large amounts of gums attached and poor mineral ligand attachment supplying 2169 mg potassium/100 grams of material. At the end of the 60 day experimental period, the animals were sacrificed and data collected as per normal laboratory procedures. The chart below gives the findings with regard to serum insulin, leptin and corticosterone, i.e., the glucocorticoid which in rats performs much the same role as does cortisol in humans.

Both of the potassium (−)-hydroxycitrate arms were superior to the calcium/potassium arm relative to control in reducing insulin, leptin and corticosterone concentrations. Because of the difficulty in achieving significance with only 5 data points per arm, calculations regarding insulin and leptin combined the data from the two KHCA arms. With respect to insulin, the one-tailed P value was a significant 0.0306, and the two-tailed P value fell slightly short of significance at 0.0612. Using this combined data, there was also a significant one-tailed P value difference between the two KHCA arms and the result found with the CaKHCA. With respect to leptin, the two KHCA arms were combined, in part, because of one anomalously high data point and yielded a one-tailed P value which was a significant 0.0241 and a two-tailed P value which was significant at 0.0482. Corticosterone results were highly significant even at 5 data points per arm. KHCA 1 was easily significantly superior to control: the one-tailed P value was a highly significant 0.0048, and the two-tailed P value was a highly significant 0.0096.

| Group | Insulin ng/mL | Leptin ng/mL | Corticosterone ng/mL |
| --- | --- | --- | --- |
| Control | 2.655 | 9.52 | 269.38 |
| Control | 7.077 | 18.94 | 497.87 |
| Control | 4.280 | 34.34 | 265.71 |
| Control | 9.425 | 24.32 | 209.54 |
| Control | 3.798 | 8.40 | 116.12 |
| KHCA 1 | 3.880 | 9.93 | 45.79 |
| KHCA 1 | 4.399 | 7.31 | 33.10 |
| KHCA 1 | 3.181 | 9.25 | 65.57 |
| KHCA 1 | 3.210 | 24.36 | 55.40 |
| KHCA 1 | 3.639 | 9.07 | 84.62 |
| KHCA 2 | 4.427 | 9.13 | 26.02 |
| KHCA 2 | 4.301 | 9.75 | 270.83 |
| KHCA 2 | 3.245 | 8.00 | 45.44 |
| KHCA 2 | 3.695 | 9.16 | 45.63 |
| KHCA 2 | 2.053 | 8.26 | 38.04 |

The findings with regard to serum insulin levels from this trial are at variance with those found in the published literature, but then again almost all such data in past trials has been based upon young animals fed a 70% glucose (as energy) or other similar diet to encourage lipogenesis. A glucose disposal agent which acts at least in part by improving peripheral insulin sensitivity and peripheral disposal of blood glucose in lean tissues will simply be overwhelmed by such a diet once available storage had been filled.

Roche and other past HCA researchers never examined leptin nor corticosterone levels. The novel findings shown here with regard to the reduction in glucocorticoid levels are quite striking and led the inventors to question if there might be physiological effects from HCA supplementation which had been overlooked in the past.

EXAMPLE 2

Effects Upon Body Protein and Mineral Content Using Middle-Aged Rats and a Moderately High Fat Diet Using the animal experiment described in Example 1, the inventors examined areas which might reasonably be expected to reflect the lowered serum corticosterone levels discovered in this trial. The two most accessible findings concerned body protein and mineral content. However, it quickly became apparent that HCA exhibits powerfully dose-dependent responses which depend both upon the total mount of the compound ingested and the form in which it is supplied. It turned out to be the case that inappropriately low doses have an effect which is the reverse of that expected and that found with adequate dosages.

The biphasic dose response issue on a diet supplying a nontrivial percentage of its calories as fat apparently has not been properly explored before. In this example, the salts supplied to all three active arms contained the same amounts of HCA. Strikingly, the apparently lower availability of HCA for physiologic uptake or usage when delivered in the form of CaKHCA emerged despite the widespread assertion among commercial suppliers of HCA products that issues of bioavailability are adequately addressed simply by making the calcium salt of the compound soluble. Such is not the case. Similarly, the lower quality potassium salt, KHCA 2, in which inadequate amounts of potassium were available to fully occupy all bonding sites, proved to be no better, but also no worse, than placebo as a weight loss agent. Only the relatively clean and relatively fully reacted KHCA 1 showed any positive effect upon food consumption and weight gain in this model. (This data can be found fully in our co-pending U.S. Patent Application, "Correcting Polymorphic Metabolic Dysfunction with (−)-Hydroxycitric Acid.")

As can be seen in the following chart, at the level of intake used experimentally on a 30% fat diet, potassium HCA salts increased both protein and minerals (ash) as percentages of body weight while reducing fat as a percentage of body weight. The CaKHCA salt, in contrast, increased fat and reduced both protein and ash as percentages of body weight. The relatively higher rates of body hydration found in the potassium salt-fed arms primarily represent elevated glycogen stores in muscle, an expected finding supported by Example 3 below.

| Mean | Control wet/dry % | CaKHCA wet/dry % | KHCA 1 wet/dry % | KHCA 2 wet/dry % |
|---|---|---|---|---|
| % Body H$_2$O | 56.70 | 56.06 | 59.96 | 58.93 |
| % Protein | 18.66/43.33 | 17.77/40.68 | 18.95/47.34 | 20.07/48.98 |
| % Fat | 20.42/46.91 | 22.56/51.04 | 17.83/44.51 | 18.27/44.37 |
| % Ash | 2.98/6.87 | 2.37/5.42 | 3.04/7.65 | 2.61/6.37 |

Because body water content distorts the true impact of the various HCA salts upon protein, fat and ash in comparison with control, calculations are also given in terms of dry weight percentages. It should be noted that both KHCA arms increased protein in comparison with control quite markedly. With regard to mineral content, findings were mixed. The non-fully reacted KHCA 2 arm was not superior to control with regard to mineral content. However, the fully reacted KHCA 1 arm caused a fairly striking increase in mineral content. Our interpretation of these results is that (1) non-fully reacted HCA can attach to minerals as a chelator and perhaps lead to reduced uptake in the gut; and (2) when used properly, HCA reduced the bone and lean tissue loss found in control due to the stress of being intubated twice daily and being subjected to normal laboratory animal arrangements. In the case of the CaKHCA arm, poor availability led to reverse effects which are yet to be fully explained. Nevertheless, the clear and novel implication of this example is that HCA might be employed to reduce mineral and tissue loss. The most likely explanation in the light of Example 1 is an effect upon glucocorticoid metabolism, which suggests that the benefits reported here will translate into improved wound healing and improved rates of tissue repair more generally in the face of stress and other causes of elevated glucocorticoid levels.

EXAMPLE 3

Effects Upon Body Protein and Mineral Content Using Young Rats and a High Sugar Diet No prior literature suggests that HCA might be useful in preventing tissue and mineral loss such as that found in osteoporosis and in individuals exposed to chronic stress. However, results similar to those found in Example 2 have been published before, albeit the researchers in question merely treated the increase in protein and ash as percentages of body composition as curiosities. In this experiment, female Zucker lean (Fa/−) and obese (Fa/fa) rats 10 weeks old, 7–8 per arm, were fed HCA as the trisodium (−)-hydroxycitrate salt as a dietary component (52.6 mmol/kg diet) which otherwise consisted of 70% glucose and 1% corn oil for six weeks. (Greenwood M R, et al. Effect of (−)-hydroxycitrate on development of obesity in the Zucker obese rat. Am J Physiol. January 1981;240(1):E72–8.) The results are found below; no dry weight data are available.

| Mean | Control Lean wet/dry % Obese wet/dry % | Tri-NaHCA Lean wet/dry % Obese wet/dry % | Pair-Fed Lean wet/dry % Obese wet/dry % |
|---|---|---|---|
| % Body H$_2$O | 60.0 23.5 | 64.3 25.8 | 58.3 25.7 |
| % Protein | 21.0/NA 10.7/NA | 22.0/NA 11.8/NA | 20.5/NA 10.9/NA |
| % Fat | 14.4/NA 63.4/NA | 8.05/NA 59.8/NA | 16.6/NA 60.9/NA |
| % Ash | 4.6/NA 2.4/NA | 4.9/NA 2.6/NA | 4.6/NA 2.6/NA |

These data are quite interesting. There is a clear trade-off between carcass fat content and carcass water content. Just as in Example 2, HCA in these animals, especially in the Zucker lean arm, increased total body water. Our best guess is that the increased water content represents increased glycogen stores. Further support for this hypothesis comes from the fact that the higher carbohydrate diet led to higher values for carcass water, albeit this conclusion is tenuous given the fact that different strains of rats were used in Example 2 and Example 3. In this example, trisodium (−)-hydroxycitrate increased carcass protein and ash/mineral content in the lean and the obese animals in comparison with control. Therefore, this data published some twenty years ago by Roche researchers would seem to support the results which the inventors found more recently with different animals and a different diet. Again, the most likely explanation in the light of Example 1 is an effect upon glucocorticoid metabolism, which suggests that the benefits reported here will translate into improved wound healing and improved rates of tissue repair more generally in the face of stress and other causes of elevated glucocorticoid levels.

EXAMPLE 4

Effects Upon Skin Health and Psoriasis, Markers for Melatonin and Growth Hormone Regulation The results in the above examples led us to question whether HCA might be useful as a supplement for individuals not in need of weight loss and not under obvious stress. To this end, a middle-aged male subject ingested approximately 2 to 3 grams HCA in the form of the potassium salt twice daily for 10 days. He was instructed to report on effects other than those which were to be expected, i.e., effects other than appetite control. Two quite interesting findings typical of re-regulation of corticoid metabolism emerged from this crude trial.

First, the subject noticed that his skin tone had improved markedly before the first week had passed. The skin had tightened and its thickness improved, pore size was reduced, the coloration of the skin on his face had become more even and it exhibited much reduced areas of inflammation or irritation. These effects were similar in kind, although greater in degree, than this subject had experienced in the past when experimenting with relatively large dosages of melatonin (5 to 20 mg taken at bedtime) and, when much younger, amino acid supplementation designed to improve growth hormone release. We interpreted this finding as indicative of the normalization of melatonin and growth hormone metabolism. None of the side effects typical of elevated melatonin supplementation, such as morning grogginess or nasal congestion, were noted.

Second, this subject noticed an improvement in his psoriasis during the last few days of the trial. In this subject's past experience, supplements which tended to improve his overall immune response and skin tone—including melatonin—at the same time tended to worsen his psoriasis. Therefore, this subject's experience with HCA was in line with the reports in the published literature regarding the condition as representative of corticoid and circadian dysregulation.

EXAMPLE 5

Numerous methods can be given as means of delivering HCA as required by the invention. The following preparation will provide a stable and convenient dosage form.

| | Ingredient | Weight | Percent | 1 Kg Batch |
|---|---|---|---|---|
| 1. | Aqueous Potassium Hydroxycitrate | 500 gm | 62.5% | 0.63 |
| 2. | Calcium Carbonate | 50 gm | 6.25% | 0.06 |
| 3. | Potassium Carbonate | 50 gm | 6.25% | 0.06 |
| 4. | Anhydrous Lactose | 150 gm | 18.75% | 0.19 |
| 5. | Cellulose Acetate Pthalate Acetate | 50 gm | 6.25% | 0.06 |
| | Total | 800 gm | 100.00% | 100.00 |

A. Blend items 1–5 in mixing bowl until smooth and even.
B. Take the liquid and spray into spray-drying oven at 300° C. until white powder forms. When powder has formed, blend with suitable bulking agent, if necessary, and compress into 800 mg tablets with hardness of 10–15 kg. This will mean that each tablet, if starting with 62% KHCA polymer powder, will have about 31% KHCA. However, if the tablets are pressed to 1600 mg, the dose will be equal to 800×62% KHCA.
C. After pressing the granulate through the screen, make sure that it flows well and compress into oblong tablets.
D. Tablets should have a weight of 1600 mg and a hardness of 14±3 kg fracture force. When tablets are completed, check for disintegration in pH 6.8, 0.05M KH2PO4. Disintegration should occur slowly over 4–5 hours.

CONCLUSIONS (−)-Hydroxycitrate has a multitude of metabolic functions. The literature teaches that the compound reduces blood lipids, induces weight loss and decreases appetite in both animals and humane. However, the inventors have discovered that HCA supplementation constitutes a novel means of reducing age-related, stress-related and other forms of glucocorticoid dysregulation. Supplementation improves wound healing and immunomodulation/immunoregulation, including improving depressed immune function and also reducing excessive immune activity such as is found in elevated humoral immunity linked to allergies and autoimmune diseases. Further evidence suggests that HCA improves melatonin metabolism with its concomitant effects upon growth hormone release through non-serotogenic mechanisms. These action by HCA have not heretofore been recognized. The benefits of HCA are especially pronounced with the use of the preferred salt of the acid, potassium hydroxycitrate, and may be further potentiated by the use of a controlled-release form of the compound. The discovery that HCA has stress-moderating and immunomodulating effects allows for the creation of novel and more efficacious approaches for improving healing (for instance, of diabetic skin ulcers) even in the face of diet and exercise habits which are less than ideal and in the face of chronic stress. Furthermore, this discovery makes possible the development of adjuvant modalities which can be used to improve the results realized through the employment of more conventional remedies.

We claim:

1. A method for preventing, treating or ameliorating chronically nonhealing wounds in individuals in need thereof which is comprised of administering orally an effective amount of (−)-hydroxycitric acid or (−)-hydroxycitric acid lactone, the alkali metal salts potassium or sodium (−)-hydroxycitrate, the alkaline earth metal salts calcium or magnesium (−)-hydroxycitrate, a mixture the alkali metal salts and/or the alkaline earth metal salts of (−)-hydroxycitrate or some mixture of alkali metal salts and alkaline earth metal salts of (−)-hydroxycitrate or in the form of the therapeutically effective amide or ester derivatives of (−)-hydroxycitric acid.

2. The method of claim 1 where the (−)-hydroxycitric acid is supplied as a therapeutically effective amount of the free acid or its lactone.

3. The method of claim 1 where the (−)-hydroxycitric acid is supplied as a therapeutically effective amount of the alkali metal salts potassium or sodium (−)-hydroxycitrate.

4. The method of claim 1 where the (−)-hydroxycitric acid is supplied as a therapeutically effective amount of the alkaline earth metal salts calcium or magnesium (−)-hydroxycitrate.

5. The method of claim 1 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

6. The method of claim 1 where the (−)-hydroxycitric acid is supplied as a therapeutically effective amount as the free acid, its lactone or as one or more of the salts or other derivatives of the free acid and is delivered in a controlled release form.

7. A method for modulating immune response in individuals in need thereof which is comprised of administering orally an effective amount of (−)-hydroxycitric acid or (−)-hydroxycitric acid lactone, the alkali metal salts potassium or sodium (−)-hydroxycitrate, the alkaline earth metal salts calcium or magnesium (−)-hydroxycitrate, a mixture the alkali metal salts and/or the alkaline earth metal salts of (−)-hydroxycitrate or some mixture of alkali metal salts and alkaline earth metal salts of (−)-hydroxycitrate or in the form of the therapeutically effective amide or ester derivatives of (−)-hydroxycitric acid.

8. The method of claim 7 where the (−)-hydroxycitric acid is supplied as a therapeutically effective amount of the free acid or its lactone.

9. The method of claim 7 where the (−)-hydroxycitric acid is supplied as a therapeutically effective amount of the alkali metal salts potassium or sodium (−)-hydroxycitrate.

10. The method of claim 7 where the (−)-hydroxycitric acid is supplied as a therapeutically effective amount of the alkaline earth metal salts calcium or magnesium (−)-hydroxycitrate.

11. The method of claim 7 where the (−)-hydroxycitric acid is supplied as a therapeutically effective amount of a mixture the alkali metal salts and/or the alkaline earth metal salts of (−)-hydroxycitrate or some mixture of alkali metal salts and alkaline earth metal salts of (−)-hydroxycitrate or in the form of therapeutically effective amide and/or ester derivatives of (−)-hydroxycitric acid.

12. The method of claim 7 where the (−)-hydroxycitric acid is supplied as a therapeutically effective amount as the free acid, its lactone or as one or more of the salts or other derivatives of the free acid and is delivered in a controlled release form.

* * * * *